United States Patent [19]

Bestmann et al.

[11] 4,118,406
[45] Oct. 3, 1978

[54] PROCESS FOR PREPARING CIS-OLEFINS

[75] Inventors: Hans Jürgen Bestmann, Erlangen; Werner Theo Stransky; Otto Vostrowsky, both of Uttenreuth, all of Fed. Rep. of Germany

[73] Assignee: Hoechst Aktiengesellschaft, Frankfurt am Main, Fed. Rep. of Germany

[21] Appl. No.: 823,102

[22] Filed: Aug. 8, 1977

Related U.S. Application Data

[60] Division of Ser. No. 671,417, Mar. 29, 1976, Pat. No. 4,057,593, which is a continuation of Ser. No. 521,170, Nov. 5, 1974, abandoned.

[30] Foreign Application Priority Data

Nov. 7, 1973 [DE] Fed. Rep. of Germany ....... 2355534

[51] Int. Cl.$^2$ .................. C11C 3/02; C07C 29/00; C07C 1/00
[52] U.S. Cl. .................. 260/410.9 R; 260/682; 260/680 R; 260/677 R; 560/238; 560/261; 568/857; 568/878
[58] Field of Search .................. 260/410.9 R, 638 R, 260/682, 680 R, 677 R; 560/238, 261

[56] References Cited

U.S. PATENT DOCUMENTS

| | | | |
|---|---|---|---|
| 3,634,518 | 1/1972 | Buddrus | 560/238 |
| 3,706,733 | 12/1972 | Henrick | 560/261 |
| 3,732,282 | 5/1973 | Henrick et al. | 260/410.9 R |
| 3,816,484 | 6/1974 | Henrick et al. | 260/638 R |

OTHER PUBLICATIONS

Noller; Chemistry of Organic Compounds 3rd Ed. Philadelphia (1965) pp. 535–538.
Organic Reactions vol. 14, Chapter 3 (1965).

*Primary Examiner*—Winston A. Douglas
*Assistant Examiner*—John F. Niebling
*Attorney, Agent, or Firm*—Curtis, Morris & Safford

[57] ABSTRACT

A process for preparing cis-olefins of the formula

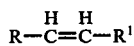

where R ia alkyl or alkenyl and R$^1$ is alkyl and alkenyl, both optionally substituted by hydroxy, carbalkoxy or acyloxy, which comprises an ylide solution of the compound R—CH$_2$—P$^\oplus$(C$_6$H$_5$)$_3$Br$^\ominus$ in hexaalkyl phosphoric acid traimide and adding an aldehyde of the formula R$^1$—CHO.

14 Claims, No Drawings

PROCESS FOR PREPARING CIS-OLEFINS

This is a division of application Ser. No. 671,417, filed Mar. 29, 1976 now U.S. Pat. No. 4,057,593 which in turn is a continuation of application Ser. No. 521,170 filed Nov. 5, 1974, now abandoned.

Stereospecific syntheses of olefins according to Wittig's reaction by means of salt-free ylides are already known (see: Angew. Chem. 78 (1966), 677). Such ylide solutions had to be prepared hitherto according to the technically complicated sodium-amide method (Liebigs Ann. Chem. 619, (1958), 10; Angew. Chem. 77 (1965), 609).

The present invention provides an improved process for preparing cis-olefins of the formula $$R-\overset{H}{C}=\overset{H}{C}-R^1, \qquad III$$

wherein
R is straight-chain or branched ($C_1$-$C_{15}$)alkyl or ($C_2$-$C_{15}$) alkenyl and
$R^1$ is a straight-chain or branched ($C_1$-$C_{20}$) alkyl or ($C_2$-$C_{20}$) alkenyl group both being optionally substituted in 3-position or in farther position relative to the aldehyde group by hydroxy, lower carbalkoxy or ($C_1$-$C_3$) acyloxy, which comprises dissolving an alkali metal or alkaline earth metal in a hexaalkylphosphoric acid triamide, adding to the solution obtained a phosphonium salt of the formula $$R-CH_2-P^{\oplus}(C_6H_5)_3Br^{\ominus}, \qquad I$$

and adding to the reaction mixture obtained an aldehyde of the formula $$R^1-C\overset{\displaystyle O}{\underset{\displaystyle H}{\diagdown}} \qquad II$$

and isolating the product obtained by known methods.

Suitable alkali metals or alkaline earth metals are preferably lithium, sodium and magnesium, especially potassium, furthermore calcium, strontium and baryum.

The alkyl groups in the hexaalkylphosphoric acid triamide may be identical or different and have preferably from 1 to 4, especially 1 or 2 carbon atoms. The well-known easily obtainable hexamethylphosphoric acid triamide is especially preferred.

The process is generally carried out as follows: Crushed alkali metal or alkaline earth metal is introduced under nitrogen atmosphere into the hexaalkylphosphoric acid triamide while stirring or shaking, whereby the original blue color of the solution turns reddish-brown. For reasons of simplicity the dissolution is effected at room temperature, but may be carried out generally at temperatures of from 10° to 80° C., preferably from 15° to 30° C. When the alkaline earth metal or alkali metal has dissolved completely after approximately 1 to 3 hours, an equivalent quantity or optionally an excess of up to 20%, preferably up to 10% of a phosphonium salt of formula I, wherein R preferably contains up to 10 carbon atoms, is added to the solution. The phosphonium salts may be obtained by known processes for instance by reacting corresponding α-bromosubstituted compounds with triphenyl phosphine. The phosphonium salt may be added as such or preferably in the form of a suspension in hexamethylphosphoric acid triamide. The quantity of hexamethylphosphoric acid triamide required per millimole of phosphonium salt or per milliequivalent of alkali metal or alkaline earth metal is generally in the range from 0.5 to 5 ml or more, preferably from 0.8 to 2 ml. The upper limit is not critical.

An aldehyde of formula II is then added to the ylide solution obtained. In these aldehydes R' preferably contains 2 to 15 carbon atoms and may be substituted (preferably in terminal position by hydroxy, lower carbalkoxy or lower acyloxy, preferably a formyloxy or acetoxy group.

The reaction mixture is stirred at the chosen reaction temperature until the reaction is complete (at room temperature after about 8 to 15 hours). The olefin formed is isolated in known manner, for example by distillation or, in the case of higher boiling compounds, by pouring on ice and subsequent extraction.

The aldehyde may as well be prepared in situ by oxidizing the ylide solution, for example by means of dry oxygen. In this manner symmetric cis-olefins of the formula $$R-\overset{H}{C}=\overset{H}{C}-R \qquad IIIa$$

are obtained, having a degree of purity of more than 95% according to gaschromatographic and spectroscopic analyses. They are valuable intermediates for organic syntheses and a series of these compounds has a pheromone effect on a number of lepidoptera.

The following examples illustrate the invention.

EXAMPLE 1

Preparation of Ylide Solution

Finely cut potassium was introduced in absolute hexamethylphosphoric acid triamide under a nitrogen atmosphere. The dark blue solution obtained heated after about 15 minutes turning reddish-brown. After 1 to 3 hours, when the potassium was completely dissolved, a suspension of an equivalent quantity of a phosphonium salt of formula I in absolute hexamethylphosphoric acid triamide was added.

EXAMPLE 2

Preparation of cis-octene (4)

A ylide solution was prepared from 2.2 g (55 millimoles) of potassium and 20 g (50 millimoles) of triphenyl-n-butyl phosphonium bromide in 100 ml of hexamethylphosphoric acid triamide according to example 1 and 4.0 g (55 millimoles) of butyraldehyde was added. After 12 hours the octene(4) obtained was distilled from the reaction solution. It was taken up in pentane, the solution washed subsequently with diluted sulfuric acid, sodium hydrogen sulfite and water and dried with sodium sulfate. The pentane was removed from the octene(4) by distilling it over a Vigreux column. The remaining crude product was distilled.

Boiling point$_{760}$ = 120° C.
Yield: 4.3 g = 76%.

EXAMPLE 3

Preparation of cis-octane(4) by autoxidation

Dry oxygen was passed through an ylide solution preapared in an analogous manner to example 2. The batch was worked up as in example 2.

Boiling point$_{760}$ = 120° C.
Yield: 2.0 g = 70%

EXAMPLE 4

Preparation of cis-9-alkenol-1-acetates

An ylide solution was prepared from 0.94 g (24 millimoles) of finely cut potassium in about 50 ml of absolute hexamethylphosphoric acid triamide and 24 millimoles of triphenylethyl phosphonium bromide. The dimethylamine formed in this process was removed in vacuo as far as possible while excluding humidity. After stirring for 4 hours 20 millimoles (4.0 g) of 9-acetoxynonanal were added while cooling with water, the whole was stirred over night and the reaction mixture was poured on ice water acidified with a small quantity of diluted sulfuric acid.

The unsaturated ester was extracted with n-hexane. The combined hexane extracts were washed with diluted sulfuric acid in order to remove small quantities of hexamethylphosphoric acid triamide. Unreached aldehyde was separated from the unsaturated ester via the hydrogensulfite addition compound and triphenylphosphine formed during the reaction via triphenylmethyl phosphonium iodide. Small quantities of triphenyl phosphine oxide extracted by n-hexane completely cristallized during the night at about −25° C. and were filtered off with suction. After drying the n-hexane was removed in vacuo and the colourless oily residue was distilled.

The yield was 2.2 g (50%) of cis-9-undecenol-1-acetate. Boiling point$_{0.01}$ 84° C.

In the same manner a number of other compounds having pheromone effect on various lepidoptera were prepared by varying R, for example,

| cis-9-dodecenol-1-acetate | boiling point$_{0.1}$ | 101 – 102° C |
|---|---|---|
| (R = n-propyl) | yield | 2.3 g (51%). |

This compound has a repellent effect on males of the pine shoot moth (*Evetria buoliana* Schiff.) and is the sexual attractant of males of *Paralobesia viteana*.

| cis-9-tridecenol-1-acetate | boiling point$_{0.01}$ | 97° C |
|---|---|---|
| (R = n-butyl) | yield | 2.6 g (54 %) |
| cis-tetradecenol-1-acetate | boiling point$_{0.01}$ | 102 – 104° C |
| (R = n-pentyl) | yield | 2.6 g (51 %) |

This compound is the sexual attractant of females of *Spodoptera frugiperda*, as well as a component of the pheromone of *Adoxophyes orana*.

| cis-9-pentadecenol-1-acetate | boiling point$_{0.01}$ | 118° C |
|---|---|---|
| (R = n-hexyl) | yield | 2.8 g (57 %) |

EXAMPLE 5

Preparation of cis-11-alkenol-1-acetates

These substances were prepared in an analogous manner as in example 4, by using 4.6 g (20 millimoles) of 11-acetoxyundecanal instead of 9-acetoxynonanal.

The following compounds having a pheromone effect were obtained:

| cis-11-tridecenol-1-acetate | boiling point$_{0.01}$: | 101° C |
|---|---|---|
| (R = n-ethyl) | yield: | 2.5 g (52%) |
| cis-11-tetradecenol-1-acetate | boiling point$_{0.15}$: | 103° C |
| (R = n-propyl) | yield: | 2.3 g (45%) |

This compound is the sexual attractant of the females of *Argyrotaenia velutinana, Choristoneura rosaceana, Ostrinia nubilalis, Ancylis spectrana, Zeiraplera diviana* and a component of the pheromone of *Adoxophyses orana*. It also has an attracting effect on cabbage moth.

| cis-11-hexadecenol-acetate | boiling point$_{0.1}$: | 108° C |
|---|---|---|
| (R = n-pentyl) | yield: | 2.6 g (47 %) |

EXAMPLE 6

Preparation of cis-9-tetradecene-ol-1-formiate 3.8 g of 9-formyloxynonanal were added to an ylide solution of 0.94 g of potassium and 9.3 g of n-pentyl-triphenyl phosphonium bromide prepared according to example 4. After stirring for 12 hours the mixture was worked up as in example 4.

The yield was: 2.5 g (52%) of cis-9-tetradecene-ol-1-formiate.

Boiling point$_{0.01}$: 97° to 100° C.

The compound had an attracting effect on males of *Heliothis zea*.

EXAMPLE 7

Preparation of 2-methyl-cis-7-octadecene 0.94 g (24 millimoles) of finely cut potassium in about 50 ml of absolute hexamethylphosphoric acid triamide were reacted with 10.92 g (24 millimoles) of isooctylphenyl phosphonium bromide giving the corresponding ylide, this was then reacted with 3.8 g (20 millimoles) of n-undecanal giving the olefin. The whole was worked up as in example 4.

The yield was 2 g (37%) of 2-methyl-cis-7-octadecene, boiling point: 125° to 129° C./0.2 mm Hg.

When reacting this compound with m-chlorobenzoic acid the corresponding cis-epoxide was obtained, the sexual attractant of the great gipsy moth (Lymantria dispar).

EXAMPLE 8

Preparation of cis-9-trans-12-tetradecadienol-1-acetate 4.0 g of acetoxynonanal was added dropwise to an ylide solution prepared according to example 4 by using (E-3-pentenyl)-triphenyl phosphonium bromide. The mixture was stirred for 12 hours at room temperature and worked up as in example 4.

Yield: 2.1 g (43%) of cis-9-trans-12-tetradecadienol-1-acetate, boiling point$_{0.04}$ 110° to 112° C.

This compound is the sexual attractant of the females of *Plodia interpunctuella, Anagasta kühniella* and *La-*

*phygma exigua.* It is moreover a component of the pheromone of *cadra cutella* and *prodenia eridiana.*

EXAMPLE 9

Preparation of cis-9-unsaturated propionates and butyrates

The preparation was carried out as in example 4, but using, instead of the 9-acetoxynonanal, either 3.96 g (20 millimoles) of 9-oxynonyl-1-propionate or 4.24 g (20 millimoles) of 9-oxynonyl-1-butyrate. The following compounds were obtained:

| | |
|---|---|
| cis-9-dodecenyl-1-propionate boiling point$_{0.05}$ 96–97° C | yield 2.83 g (62 %) |
| cis-9-tetradecenyl-1-butyrate boilingpoint$_{0.01}$ 118 – 121° C | yield 2.97 g (55 %) |

EXAMPLE 10

Preparation of 9-unsaturated Carboxylic Acid Methyl Esters

The corresponding ylide solutions were reacted with 9-oconanoic acid methyl ester (3.4 g, 20 millimoles) as in example 4. The following substances were obtained:

| | |
|---|---|
| cis-9-dodecenoic acid methyl ester boiling point$_{0.03}$ 82–83° C yield 2.08 g (49 %) | |
| cis-9-trans-12-tetradecadienoic acid methyl ester boiling point$_{0.05}$ 97–99° C yield 2.34 g (50 %) | |

What is claimed is:

1. An improved process for preparing a cis-olefin of the formula $$R-\overset{H}{C}=\overset{H}{C}-R^1, \quad \text{III}$$

wherein
R is straight-chain or branched ($C_1$–$C_{15}$) alkyl or ($C_2$–$C_{15}$) alkenyl and
$R^1$ is a straight-chain or branched ($C_1$–$C_{20}$) alkyl or ($C_2$–$C_{20}$) alkenyl group further substituted in the 3-position or in a position more remote from the aldehyde group in Formula II by hydroxy, lower carbalkoxy or ($C_1$–$C_3$) acyloxy,
which comprises dissolving sodium or potassium in a hexaalkylphosphoric acid triamide, adding to the solution obtained a phosphonium salt of the formula $$R-CH_2-P^{\oplus}(C_6H_5)_3 BR^{\ominus}, \quad \text{I}$$

adding to the reaction mixture obtained an aldehyde of the formula $$R^1-C\overset{\displaystyle\nearrow O}{\underset{\displaystyle\searrow H}{}} \quad \text{II}$$

and isolating the product obtained.

2. The process defined in claim 1 in which potassium is dissolved in a hexaalkylphosphoric acid triamide.

3. The process defined in claim 1 in which sodium is dissolved in a hexaalkylphosphoric acid triamide.

4. The process defined in claim 1, wherein the hexaalkylphosphoric acid triamide used is hexamethylphosphoric acid triamide.

5. A process for preparing symmetric cis-olefins of the formula $$R-\overset{H}{C}=\overset{H}{C}-R$$

which comprises introducing oxygen into the ylide solution obtained according to claim 1.

6. Process as defined in claim 1, wherein the alkyl groups in the hexaalkylphosphoric acid triamide have from 1 to 4 carbon atoms.

7. Process as defined in claim 2, wherein the potassium is dissolved at a temperature generally ranging from 10° to 80° C., the phosphonium salt is added in an excess ranging from about 0 to 20%, and R contains up to 10 carbon atoms.

8. Process as defined in claim 1, wherein the cis-olefin formed is isolated by distillation.

9. Process as defined in claim 1, wherein the cis-olefin formed is isolated by pouring on ice and subsequent extraction.

10. Process as defined in claim 6, wherein the cis-olefin formed is isolated by distillation.

11. Process as defined in claim 6, wherein the cis-olefin formed is isolated by pouring on ice and subsequent extraction.

12. The process defined in claim 1, wherein the hexaalkylphosphoric acid triamide used has an alkyl group of from 1 to 4 carbon atoms.

13. The process defined in claim 3, wherein the sodium is dissolved at a temperature generally ranging from 10° to 80° C., the phosphonium salt is added in an excess ranging from about 0 to 20%, and R contains up to ten carbon atoms.

14. A process for making cis-olefins with at least 95 weight % purity according to the method of claim 1.

* * * * *